United States Patent
Schwarz et al.

(10) Patent No.: US 6,861,069 B2
(45) Date of Patent: Mar. 1, 2005

(54) PRODUCTION OF A DIRECTLY COMPRESSIBLE TABLETTING AID

(75) Inventors: Eugen Schwarz, Darmstadt (DE); Gernot Möschl, Darmstadt (DE); Karin Maul, Darmstadt (DE)

(73) Assignee: Merck Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 09/529,543

(22) PCT Filed: Oct. 2, 1998

(86) PCT No.: PCT/EP98/06272

§ 371 (c)(1),
(2), (4) Date: Apr. 14, 2000

(87) PCT Pub. No.: WO99/18935

PCT Pub. Date: Apr. 22, 1999

(65) Prior Publication Data

US 2003/0039684 A1 Feb. 27, 2003

(30) Foreign Application Priority Data

Oct. 15, 1997 (DE) .......................... 197 45 265

(51) Int. Cl.$^7$ ............................ A61K 9/14; A61K 9/20; A61K 9/26; A61K 9/46; B20C 59/00
(52) U.S. Cl. ...................... 424/464; 264/117; 264/118; 424/464; 424/465; 424/466; 424/469; 424/470; 424/489
(58) Field of Search ................................ 424/464, 470, 424/489, 465, 469, 466; 264/117, 118

(56) References Cited

U.S. PATENT DOCUMENTS

| 5,139,795 A | | 8/1992 | Duross ........................ 426/3 |
| 5,158,789 A | | 10/1992 | Duross ........................ 426/3 |
| 5,204,115 A | * | 4/1993 | Olinger et al. .............. 424/470 |
| 5,536,526 A | * | 7/1996 | Virtanen et al. ............ 426/658 |
| 5,576,014 A | * | 11/1996 | Mizumoto et al. .......... 424/435 |
| 5,958,471 A | * | 9/1999 | Schwarz et al. ............... 426/3 |
| 6,274,727 B1 | * | 8/2001 | Maul et al. ................. 536/127 |

FOREIGN PATENT DOCUMENTS

| EP | 0306454 | | 3/1989 |
| EP | 0329977 | | 8/1989 |
| JP | 02000086537 A | * | 3/2000 |
| WO | 9014821 | | 12/1990 |
| WO | 92 10168 | | 6/1992 |

* cited by examiner

Primary Examiner—Thurman K. Page
Assistant Examiner—S. Tran
(74) Attorney, Agent, or Firm—Millen White Zelano & Branigan, P.C.

(57) ABSTRACT

The invention relates to directly compressible tabletting aids with a xylitol content of more than 90% by weight and a content of at least one other polyol of less than 10% by weight, which are produced by co-spray drying or co-fluidized bed granulation. The invention further relates to compositions, formulations and solid forms or compacts which comprise a tabletting aid according to the invention, and to a process for producing the tabletting aids according to the invention.

10 Claims, No Drawings

PRODUCTION OF A DIRECTLY COMPRESSIBLE TABLETTING AID

The invention relates to directly compressible tabletting aids with a xylitol content of more than 90% by weight and a content of at least one other polyol of less than 10% by weight, which are produced by co-spray drying or co-fluidized bed granulation. The tabletting aids according to the invention have improved tabletting properties by comparison with xylitol, in particular in relation to the resulting tablet hardnesses, the friability and the tendency to capping. These improved tabletting properties of the tabletting aids according to the invention are evident in particular in formulations with a high content of active ingredients. In addition, the tabletting aids according to the invention have improved taste-masking properties by comparison with known polyols, and influence the sensory mouthfeel of the products in an advantageous manner. The invention further relates to compositions, formulations and solid forms or compacts which comprise a tabletting aid according to the invention, and to a process for producing the tabletting aids according to the invention.

Polyols and polyol mixtures are used on a large scale as additives and carriers inter alia for active pharmaceutical ingredients, chewable and suckable tablets and other products of the drugs industry and as compacts in the food industry. Because of its advantageous properties, there is particular interest in using xylitol as tabletting aid. Xylitol has, inter alia, sweetening properties which are comparable to those of sucrose. However, it has the advantage that it is not cariogenic. There is even evidence that xylitol is able to prevent caries. In addition, xylitol shows a cooling effect, which is felt to be pleasent, during the dissolving process.

In the production of compacts by direct compression, many polyols result in a rather unsatisfactory surface or lead to compacts with unsatisfactory hardness. Thus, the known polyols mannitol, lactitol, isomalt and xylitol show poor tabletting characteristics, resulting in low tablet hardness, capping and high friability of the tablets. Xylitol in particular shows extremely unsatisfactory results on direct compression.

If, despite this, polyols of this type are to be used for producing compacts, this usually entails the disadvantage of increased expenditure of effort. This is made clear by the example of mannitol. Mannitol is certainly used in pharmaceutical formulations despite the abovementioned disadvantages, in contrast to lactitol, isomalt and xylitol which tend not to be used for producing compacts. However, mannitol must usually be granulated or briquetted before compression with the other ingredients.

The use of polyol mixtures for producing xylitol-containing compacts is known. However, the xylilol content is usually relatively low. EP 0 528 604 A1 describes, for example, a composition of sorbitol and xylitol obtainable by co-melting, which particularly preferably contains a sorbitol:xylitol weight ratio in the range from 65:35 to 95:5. Since a large part of the xylitol in these compositions is replaced by sorbitol there is utilization of only a fraction of the advantageous properties of xylitol.

EP 0 329 977 B1 claims binders and diluents which contain 94 to 98% by weight xylitol and are suitable for producing directly compressed tablets. However, the production of these binders and diluents starts from crystalline xylitol which means, inter alia, that an increased number of working steps is necessary.

Hence there is an interest in simplifying processes for producing directly compressible polyol mixtures based on xylitol.

DE 44 39 858 A1 proposes producing by spray drying a polyol combination which consists essentially of at least two polyols with a mannitol content of less than 10% by weight. This is said to provide polyol compositions which can be produced without difficulty and whose tabletting properties and plasticity are improved by comparison with known polyols or polyol combinations. The compositions described as preferred are those compositions containing sorbitol and xylitol or sorbitol, xylitol and other polyols, and in particular sorbitol, xylitol and mannitol as polyols. The xylitol content is particularly preferably less than 50% by weight, especially preferably less than 35% by weight. It was found, inter alia, that the produced polyol compositions result in much smoother surfaces on tabletting, and that these products can be processed to chewing-gums which have better processing properties than the chewing-gum produced with conventional sorbitol or mixtures of sorbitol and other polyols. However, there is no reference in DE 44 39 858 A1 to the possibility of obtaining directly compressible tabletting aids based on xylitol, whose direct compressibility is normally very poor, using polyol combinations obtainable by spray drying and having a higher xylitol content, in particular having a xylitol content greater than 90% by weight, which aids additionally have further beneficial properties, in particular a taste masking on co-spray drying or co-fluidized bed granulation with active ingredients and an advantageous effect on the sensory mouthfeel of the products.

Problems with the taste properties experienced by the user arise in the formulation of pharmaceutical compositions for oral administration in many cases, not only for liquid administration forms. On chewing antacid tablets in particular, a chalky, soapy taste is experienced as unpleasant. Attempts have been made with little success hitherto to mask this unpleasant taste by various additives.

A problem which has also arisen with a wide variety of active ingredients is a taste which is experienced as extremely bitter. Masking of the active ingredients with particularly bitter tastes has not hitherto succeeded even by the addition of flavourings or aromatizing substances. Although it is possible to provide tablets containing such active ingredients with a coating, this method is unsuitable if rapid absorption of the active ingredient, which takes place through the oral mucosa even during chewing of the tablets, is desired.

Particular requirements must also be met by the surface of tablets intended to be sucked, such as, for example, throat tablets. In this case, it is desirable for the actual tablet to have a smooth surface which is retained during the sucking and does not gradually become rough.

Furthermore, suckable and, in particular, chewable tablets are increasingly being supplied in the area of dietary supplementation (vitamin and mineral supplementation). The carrier content in particular of tablets for mineral supplementation is very low so that the taste properties are substantially determined by the relevant mineral.

The object therefore was to provide a directly compressible tabletting aid which is simple to produce and which has improved tabletting properties by comparison with xylitol, in particular in relation to the resulting tablet hardnesses, the friability and the tendency to capping, and in addition has improved taste-masking properties by comparison with known polyols, and has an advantageous effect on the sensory mouthfeel of the products.

It has now been found that the abovementioned object of the present invention can be achieved if the tabletting aid comprises more than 90% by weight of xylitol and less than 10% by weight of at least one other polyol and is produced by spray drying or fluidized bed granulation.

The invention thus relates to a directly compressible tabletting aid which is simple to produce, comprises more than 90% by weight of xylitol and less than 10% by weight of at least one other polyol, and is produced by spray drying or fluidized bed granulation and has the following properties:

improved tabletting properties by comparison with xylitol, in particular in relation to the resulting tablet hardnesses, the friability and the tendency to capping improved taste-masking properties by comparison with known polyols and advantageous effects on the sensory mouthfeel of the products.

The term "polyol" represents sugar alcohols of the general formula

where n is 2 to 6, preferably 3 to 4, and their dimeric anhydrides, in particular $C_{12}H_{24}O_{11}$.

The term "polyols" particularly represents hexitols such as sorbitol and mannitol, pentitols such as xylitol, but possibly also $C_4$-polyalcohols such as erythritol or $C_{12}$-polyalcohols such as lactitol, maltitol or isomalt. However, besides polyols, it is also possible to employ other suitable carbohydrates.

Preferred embodiments are:

a1) Directly compressible tabletting aids obtainable by dissolving xylitol and at least one other polyol in water and spraying the resulting aqueous mixture in a stream of air at a temperature of from 120° C. to 300° C.

a2) Directly compressible tabletting aids obtainable by dissolving xylitol and at least one other polyol in water and fluidizing the resulting aqueous mixture in a stream of air at a temperature of from 30° C. to 110° C.

b) Directly compressible tabletting aids employing xylitol and mannitol, xylitol and lactitol or xylitol, mannitol and lactitol as polyols.

c) Directly compressible tabletting aids where the ratio of xylitol to mannitol is in a range between 90:10 to 98:2, in particular between 90:10 to 95:5.

d) Directly compressible tabletting aids where the ratio of xylitol to lactitol is in a range between 90:10 to 98:2, in particular between 90:10 to 95:5.

e) Directly compressible tabletting aids where the xylitol:mannitol:lactitol ratio is in a range between 90:1:9 or 90:9:1 and 98:1:1.

f) Directly compressible tabletting aids according to any of the preceding preferred embodiments a1) to e), where the water content is less than 1% by weight.

The invention further relates to compositions, formulations and solid forms or compacts comprising a tabletting aid according to the invention.

The total amount of polyol employed for producing the solid forms or compacts should be chosen such that 10% by weight to 99% by weight, in particular 25% by weight to 98% by weight, of polyol is present in the solid forms or compacts according to the invention.

These solid forms or compacts may comprise on the one hand minerals from the group of physiologically tolerated Ca, Mg, Na, K, Fe and Zn salts in an amount of from 10% by weight to 90% by weight, in particular from 25% by weight to 75% by weight, where appropriate trace elements, and one or more vitamins and, where appropriate, one or more active ingredients which possibly have a bitter taste.

The solid forms or compacts may comprise one or more active pharmaceutical ingredients. Active ingredients of this type may be, inter alia, analgesics, antacids or others. The active pharmaceutical ingredients may be present in an amount of from 0.1% by weight to 75% by weight.

The tabletting aids according to the invention are also suitable for producing shaped and unshaped polyol compositions produced by melt extrusion. These may in turn comprise active ingredients up to a content of 80% by weight.

The percent by weight data as stated in the preceding text are, of course, to be understood to mean that the total percentages by weight of the substances employed do not exceed 100% by weight.

The invention further relates to a process for producing the tabletting aids according to the invention, comprising the following steps:

a) producing an aqueous solution of xylitol and at least one other polyol, the resulting mixture having a xylitol content of more than 90% by weight based on the total polyol content, b1) spraying the resulting mixture in a stream of air at a temperature of from 120° C. to 300° C., evaporation of the water taking place, b2) fluidizing the resulting mixture in a stream of air at a temperature of from 30° C. to 110° C., evaporation of the water taking place, and c) isolating the tabletting aid.

In a particularly preferred embodiment, the tabletting aid according to the invention consists of 90 to 98% by weight, in particular 90 to 95% by weight of xylitol and 2 to 10% by weight, in particular 5 to 10% by weight of one or two polyols selected from mannitol and lactitol.

It is very particularly preferred for the tabletting aid according to the invention to comprise more than 95% by weight of xylitol and less than 5% by weight of a polyol selected from mannitol and lactitol.

An aqueous solution of xylitol and at least one other polyol is used for the co-spray drying. The solids content is previously adjusted to about 30% by weight to about 75% by weight, in particular 60% by weight to 72% by weight, preferably by mixing two or more polyol solutions in the required ratio at a temperature of up to 80° C. The spraying is carried out by atomization using nozzles, preferably using a centrifugal atomizer, in a stream of dry air which is blown in centrifugally and is heated to a temperature of from 120° C. to 300° C., preferably 130° C. to 190° C. The amount of polyol solution added and of hot air blown in is adjusted so that the substance mixture is dried to a water content of about 0.1% by weight to about 1% by weight, where appropriate in a fluidized bed. In any event, the water content should be below 1% by weight.

The polyol particles obtained by this dehydration of the polyol solution droplets are heated during the spray drying to a temperature of about 50° C. to about 70° C., while the air which is blown in cools to about the same temperature. The polyol composition is collected in containers and, after cooling, is suitable directly for producing tablets or compacts.

The co-fluidized bed granulation is carried out, for example, as described in P. Grassmann, F. Widmer, "Einführung in die thermische Verfahrenstechnik" [Introduction to Thermal Processing Technology], published by DeGruyter, Berlin 1974.

It is possible to add to the aqueous mixture before the co-spray drying or co-fluidized bed granulation for example one or more active ingredients. Active pharmaceutical ingredients may be inter alia analgesics, antacids or others. It is further possible to add to the aqueous mixture before the spray drying or fluidized bed granulation for example flavour-masking substances and, where appropriate, colorants. Suitable flavour-masking substances are, inter alia, natural or synthetic sweeteners from the group of saccharine, aspartame, acesulfame K, neohesperidine DC, sucralose, thaumatin or stevioside.

The particular mode of production by spraying or fluidizing an aqueous solution makes it possible to disperse water-insoluble and water-soluble additions such as, for example, citric acid, sweeteners, in particular acesulfame K, aspartame, saccharin, cyclamate, sucralose, neohesperidine DC, colorants and active pharmaceutical ingredients such as, for example, analgesics, antacids and the like, vitamins, minerals and, where appropriate, trace elements homogeneously in the compositions or formulations according to the invention and the solid forms or compacts produced therefrom, in particular the tablets produced therefrom. The invention likewise relates to such solid forms and compacts.

The binders to be added where appropriate are familiar to the skilled person and serve to increase the strength of the composition. Preferred binders are cellulose derivatives, in particular hydroxypropyl-methylcellulose, carboxymethylcellulose or starch.

Besides the polyol composition according to the invention, present in the compacts according to the invention are one or more ingredients selected from active pharmaceutical ingredients and substances approved under foodstuffs legislation. Preferred substances approved under foodstuffs legislation are natural, nature-identical or synthetic aromatizing substances or flavourings, vitamins, trace elements, minerals, colorants, lubricants, release agents, sweeteners, stabilizers or antioxidants. The content of these ingredients is preferably between 0.01 and 90% by weight and, in particular, between 0.1 and 70% by weight.

The compacts are produced in a manner known per se by mixing the ingredients in dry form and then tabletting.

The polyol compositions according to the invention have a number of advantageous tabletting properties:

surprisingly, it can be asserted that solid forms, in particular tablets, with considerably improved taste properties and sensory mouthfeel are obtained by the process according to the invention using the compositions according to the invention. On use of formulations with a high mineral content of up to 90%, on the one hand the tabletting properties are found to be drastically improved and, on the other hand, the produced tablets are characterized by considerably less friability during the packaging process. Moreover use of the compositions according to the invention with the same compressive force as applied to known polyol-containing formulations results in harder tablets with smoother surfaces. This improved sensory feel in the mouth which is initially experienced is also experienced on chewing or sucking because the otherwise usual chalky or, where appropriate, soapy taste is very substantially masked. However, surprisingly, there is an improvement in the taste properties not only of these mineral tablets. Formulations in which ingredients with an extremely bitter taste are incorporated are also experienced as having a considerably better taste because the bitter taste is no longer so excessively evident.

The following examples serve to explain the described and claimed invention better. However, they are by no means to be understood to restrict the scope of protection to these examples.

EXAMPLES

The tabletting characteristics of
(1) co-spray granulated xylitol in conjunction with other polyols (Examples 1 to 4),
(2) commercial xylitol grades (Comparative Example 1) and
(3) spray-granulated pure xylitol (Comparative Example 2) were compared.
Tabletting:
Unless explicitly described otherwise, in each case about 1000 tablets were produced from a total of about 500 g of material;
Equipment: EKO DMS eccentric tablet press (instrumented); supplied by Korsch
Measurements:
Tablet hardness;
20 tablets were measured and the average was formed;
Equipment: hardness tester 6D, supplied by Schleuniger
Friability
20 tablets were measured and reweighing was carried out;
Equipment: Friabilator, supplied by RWK
Tablet weight:
20 tablets were measured and the average was formed;
Equipment: Mettler AT 201 with statistics program and LCP 45 printer, supplied by Mettler Examples 1 to 4

Xylitol (manufacturer: Cerestar) was dissolved with additions of 5–10% by weight of another polyol and subjected to a spray granulation. The spray granulation was carried out as described above. The tablettability of the spray-granulated materials was then tested. 1000 tablets were produced from one granulation.

For the comparison, mechanical mixtures of the starting components were investigated for their tablettability. In this case too, 1000 tablets were produced from a mechanical mixture.

Tablets with a diameter of 11 mm were produced aiming at a tablet weight of 500 mg.

Unless explicitly described otherwise, in each case 20 tablets were measured and tested.

Example 1

Comparison of the tablettability of co-spray dried xylitol (addition: 5% by weight of lactitol (manufacturer: Purac)) and the tablettability of a mechanical mixture of identical composition

TABLE 1

Measurements for Example 1

| | Co | Me | Co | Me | Co | Me | Co | Me |
|---|---|---|---|---|---|---|---|---|
| Pressure [kN] | 4.5 | 4.5 | 10 | * | 21 | 21 | 32 | 30 |
| Tablet hardness [N] | 20 | 10 | 43 | * | 98 | 34 | 131 | 30 |
| Friability [% by wt] | 0.44 | dis | 0.11 | * | 0.08 | 65 | 0.06 | 90 |
| Tablet weight [mg] | 502 | 498 | 503 | * | 502 | 503 | 502 | 501 |

Co: co-spray drying
Me: mechanical mixing
*: severe rough running-tabletting impossible
dis: disintegration of the tablet Example 2

Comparison of the tablettability of co-spray dried xylitol (addition: 5% by weight of mannitol (manufacturer: Merck KGaA)) and the tablettability of a mechanical mixture of identical composition

TABLE 2

Measurements for Example 2

|  | Co | Me | Co | Me | Co | Me | Co | Me |
|---|---|---|---|---|---|---|---|---|
| Pressure [kN] | 5 | 5 | 9.5 | 11 | 20 | 21.5 | 32 | 30 |
| Tablet hardness [N] | 51 | <20 | 76 | <20 | 95 | <20 | 95 | <20 |
| Friability [% by wt] | 2.0 | 37 | 0.72 | 3.8 | * | dis | * | dis |

Co: co-spray drying
Me: mechanical mixing
*: not determined (frequent capping)
dis: disintegration of the tablet The tablet weight was not determined.

Example 3

Comparison of the tablettability of co-spray dried xylitol (addition: 10% by weight of mannitol (manufacturer: Merck KGaA)) and the tablettability of a mechanical mixture of identical composition

TABLE 3

Measurements for Example 3

|  | Co | Me | Co | Me | Co | Me | Co | Me |
|---|---|---|---|---|---|---|---|---|
| Pressure [kN] | 4.5 | 5 | 10 | 10 | 19.5 | 19 | 29 | 31 |
| Tablet hardness [N] | 30 | <20 | 63 | <20 | 96 | <20 | 108 | <20 |
| Friability [% by wt] | 3.2 | 11 | 0.53 | 6.5 | 0.44 | dis | 0.67 | dis |
| Tablet weight [mg] | 501 | 500 | 502 | 500 | 502 | 501 | 501 | 501 |

Co: co-spray drying
Me: mechanical mixing
dis: disintegration of the tablet

Example 4

Comparison of the tablettability of co-spray dried xylitol (addition: 5% by weight of sorbitol (manufacturer: Merck KGaA)) and the tablettability of a mechanical mixture of identical composition

TABLE 4

Measurements for Example 4

|  | Co | Me | Co | Me |
|---|---|---|---|---|
| Pressure [kN] | 21 | 20 | 31 | 30 |
| Tablet hardness [N] | 85 | 34 | 83 | 37 |
| Friability [% by wt] | 0.18 | 31 | 0.12 | 21 |
| Tablet weight [mg] | 501 | 501 | 498 | 498 |

Co: co-spray drying
Me: mechanical mixing

At lower pressures, no tabletting was possible because of severe rough running.

Examples 1 to 4 show that the tablets produced from spray-granulated xylitol have distinctly better properties than tablets derived from compression of the corresponding mechanical mixtures. The co-spray drying results in particular in considerably greater tablet hardnesses and distinctly lower friability. Co-spray granulated xylitol produced according to the invention is very suitable for direct tabletting.

Comparative Example 1

5 xylitol grades available on the market were tested for their tablettability (manufacturers: Cerestar, Roquette, Finnsugar: one sample in each case; Xyrofin: two samples)

The measurements indicated for Comparative Example 1 are the averages of the measurements for all 5 samples.

A uniform pressure of 20 kN with a tablet diameter of 11 mm was aimed at for all the examples. Compaction of the material to be compressed was scarcely possible at lower pressure. With a higher pressure, capping and a decline in the strength of the compacts occurred.

TABLE C1

Measurements for Comparative Example 1

|  | Average | Range of the measurements | $S_{rel.}$ |
|---|---|---|---|
| Tablet diameter [mm] | 11 | — | — |
| Pressure [kN] | 20 | 18–21 | n.d. |
| Tablet hardness [N] | 31.5 | 27–39 | 5 |
| Friability [% by wt] | 12 | 4–24 | 8 |

$S_{rel}$: relative standard deviation
n.d.: not determined

The tablet weight was not determined numerically because very large, intolerable variations occurred within the individual xylitol sample grades. In addition, it did not appear worthwhile to give the measured data because the individual samples had different particle structures.

During the tabletting there was frequently rough running and capping in the tabletting machine.

The tabletting tests show that all 5 xylitol grades are unsuitable for direct tabletting.

Comparative Example 2

Conventional xylitol (manufacturer: Cerestar) was dissolved without further additions and subjected to spray granulation. The spray granulation was carried out as described above. 1000 tablets were produced from one granulation.

TABLE C2

Measurements for Comparative Example 2

|  | Spray granulation in a spray drier | Spray granulation in a fluidized bed |
|---|---|---|
| Tablet diameter [mm] | 11 | 11 |
| Pressure [kN] | 20 | 20 |
| Tablet hardness [N] | 57 (range: 52–62) | 60 (range: 49–71) |
| Friability [% by wt] | 10.5 | 3 |
| Tablet weight [mg] | 510 | 460 |

The measurements show that spray-granulated pure xylitol cannot be tabletted without further additions. For a tablet with a diameter of 11 mm, the tablet hardnesses are too low and the friability is too high. The tablet weight is moreover subject to large variations within a measurement series.

What is claimed is:

1. A process for producing a directly compressible tabletting aid comprising a xylitol content of more than 90% by weight and a content of at least one other polyol of less than 10% by weight, produced by dissolving the xylitol in a solvent and spray drying or fluidized bed granulating, comprising:

a) producing an aqueous solution by dissolving xylitol and at least one other polyol, the resulting mixture having a xylitol content of more than 90% by weight based on the total polyol content, b1) spraying the resulting mixture in a stream of air at a temperature of from 120° C. to 300° C., evaporation of the water taking place, or b2) fluidizing the resulting mixture in a stream of air at a temperature of from 30° C. to 110° C., evaporation of the water taking place, and c) isolating the tabletting aid.

2. A process according to claim 1, wherein the at least one other polyol present in addition to xylitol is selected from the group consisting of mannitol and lactitol.

3. A process according to claim 1, wherein the directly compressible tabletting aid has a water content of less than 1% by weight.

4. A process according to claim 1, wherein the at least one other polyol is mannitol; lactitol; or mannitol and lactitol.

5. A process according to claim 4, wherein the ratio of xylitol to mannitol is 90:10 to 98:2.

6. A process according to claim 4, wherein the ratio of xylitol to lactitol is 90:10 to 98:2.

7. A process according to claim 4, wherein the xylitol:mannitol:lactitol ratio is between 90:1:9 or 90:9:1 and 98:1:1.

8. A process according to claim 4, wherein the ratio of xylitol to mannitol is in a range between 90:10 to 95:5.

9. A process according to claim 4, wherein the ratio of xylitol to lactitol is in a range between 90:10 to 95:5.

10. A process for producing a tablet composition, comprising:

making an aqueous solution of xylitol and at least one other polyol, the resulting solution having a xylitol content of more than 90% by weight based on the total polyol content, b1) spraying the resulting mixture in a stream of air at a temperature of 120° C.–300° C., evaporation of the water taking place, or b2) fluidizing the resulting mixture in a stream of air at a temperature of 30° C.–110° C., evaporation of the water taking place, and c) isolating the tabletting aid.

* * * * *